United States Patent
Schwinn

(10) Patent No.: US 7,829,545 B2
(45) Date of Patent: Nov. 9, 2010

(54) METHOD OF TREATING BLADDER AND LOWER URINARY TRACT SYNDROMES

(75) Inventor: Debra A. Schwinn, Durham, NC (US)

(73) Assignee: Duke University, Durham, NC (US)

(*) Notice: Subject to any disclaimer, the term of this patent is extended or adjusted under 35 U.S.C. 154(b) by 1632 days.

(21) Appl. No.: 10/268,969

(22) Filed: Oct. 11, 2002

(65) Prior Publication Data

US 2003/0134812 A1 Jul. 17, 2003

Related U.S. Application Data

(63) Continuation of application No. 09/306,013, filed on May 6, 1999, now abandoned.

(60) Provisional application No. 60/084,479, filed on May 6, 1998.

(51) Int. Cl.
| C07H 21/02 | (2006.01) |
| C07H 21/04 | (2006.01) |
| A01N 43/04 | (2006.01) |
| A61K 31/70 | (2006.01) |

(52) U.S. Cl. ....................... 514/44; 536/24.5

(58) Field of Classification Search .......... 514/44; 435/6, 325, 375; 536/23.1, 24.5
See application file for complete search history.

(56) References Cited

U.S. PATENT DOCUMENTS

| 3,994,974 A | 11/1976 | Murakami et al. |
| 4,063,065 A | 12/1977 | Wust |
| 4,145,363 A | 3/1979 | Murakami et al. |
| 4,217,305 A | 8/1980 | Imai et al. |
| 4,373,106 A | 2/1983 | Imai et al. |
| 4,558,156 A | 12/1985 | Imai et al. |
| 4,665,095 A | 5/1987 | Winn et al. |
| 4,703,063 A | 10/1987 | Imai et al. |
| 4,724,148 A | 2/1988 | Sonobe et al. |
| 4,731,478 A | 3/1988 | Niigata et al. |
| 4,761,500 A | 8/1988 | Niigata et al. |
| 4,765,988 A | 8/1988 | Sonobe et al. |
| 4,868,216 A | 9/1989 | Imai et al. |
| 4,880,841 A | 11/1989 | Imai et al. |
| 4,987,152 A | 1/1991 | Imai et al. |
| 5,063,246 A | 11/1991 | Imai et al. |
| 5,110,820 A | 5/1992 | Fujikura et al. |
| 5,198,587 A | 3/1993 | Imai et al. |

(Continued)

FOREIGN PATENT DOCUMENTS

EP 257787 3/1988

(Continued)

OTHER PUBLICATIONS

Agrawal et al., TIBTECH 1996. 14:376-387.*

(Continued)

Primary Examiner—Sean McGarry
Assistant Examiner—Terra Cotta Gibbs
(74) Attorney, Agent, or Firm—Nixon & Vanderhye P.C.

(57) ABSTRACT

The present invention relates to bladder and lower urinary tract syndromes, particularly, irrative symptoms, and to a method of treating same using $\alpha_{1d}$-adrenergic receptor ($\alpha_{1d}$AR) antagonists. The invention further relates to a method of screening compounds for their ability to serve as $\alpha_{1d}$AR selective antagonists.

2 Claims, 5 Drawing Sheets

U.S. PATENT DOCUMENTS

| | | | |
|---|---|---|---|
| 5,229,392 | A | 7/1993 | George et al. |
| 5,244,894 | A | 9/1993 | George et al. |
| 5,244,901 | A | 9/1993 | George et al. |
| 5,246,939 | A | 9/1993 | George et al. |
| 5,254,560 | A | 10/1993 | George et al. |
| 5,330,985 | A | 7/1994 | George et al. |
| 5,340,814 | A | 8/1994 | Chern et al. |
| 5,380,742 | A | 1/1995 | Sevrin et al. |
| 5,391,825 | A | 2/1995 | Niigata et al. |
| 5,403,842 | A | 4/1995 | Leonardi et al. |
| 5,403,847 | A | 4/1995 | Gluchowski et al. |
| 5,420,130 | A | 5/1995 | George et al. |
| 5,447,916 | A | 9/1995 | Spellmeyer et al. |
| 5,447,958 | A | 9/1995 | Niigata et al. |
| 5,480,871 | A | 1/1996 | Spellmeyer et al. |
| 5,503,843 | A | 4/1996 | Santus et al. |
| 5,508,306 | A | 4/1996 | Chiu et al. |
| 5,512,677 | A | 4/1996 | Chern et al. |
| 5,538,976 | A | 7/1996 | Okada et al. |
| 5,556,753 | A | 9/1996 | Bard et al. |
| 5,561,154 | A | 10/1996 | Bellamy et al. |
| 5,573,908 | A | 11/1996 | Allen et al. |
| 5,578,611 | A | 11/1996 | Gluchowski et al. |
| 5,591,757 | A | 1/1997 | Fujikura et al. |
| 5,610,174 | A | 3/1997 | Craig et al. |
| 5,714,381 | A | 2/1998 | Bard et al. |
| 5,824,680 | A | 10/1998 | Turner et al. |
| 5,861,309 | A | 1/1999 | Bard et al. |
| 2008/0026399 | A1 | 1/2008 | Schwinn |

FOREIGN PATENT DOCUMENTS

| | | |
|---|---|---|
| EP | 382 935 | 8/1990 |
| EP | 380144 | 8/1990 |
| EP | 594 484 | 4/1994 |
| EP | 0 682 028 | 3/1995 |
| EP | 675109 | 10/1995 |
| EP | 753 511 | 1/1997 |
| FR | 2 703 355 | 3/1993 |
| FR | 2 703 355 | 10/1994 |
| FR | 2 724 382 | 3/1996 |
| FR | 2 724 383 | 3/1996 |
| JP | 72021421 | 6/1972 |
| JP | 72027091 | 7/1972 |
| JP | 73001069 | 1/1973 |
| JP | 73001070 | 1/1973 |
| JP | 74011218 | 3/1974 |
| JP | 49051258 | 5/1974 |
| JP | 49051271 | 5/1974 |
| JP | 54061139 | 5/1979 |
| JP | 6-501713 | 2/1994 |
| JP | 8126491 | 5/1996 |
| WO | WO 94/14769 | 7/1994 |
| WO | WO 95/19357 | 7/1995 |
| WO | WO 96/40136 | 12/1996 |
| WO | WO 97/42956 | 11/1997 |
| WO | WO 99/57131 | * 11/1999 |

OTHER PUBLICATIONS

Braasch, D. A. Biochemistry. Apr. 2002; 41(14): 4503-4510.*

Branch, A. D. ,Trends Biochem Sci. Feb. 1998;23(2):45-50.*

Gewirtz et al., Proc. Natl. Acad. Sci. 1996. v 93, pp. 3161-3163.*

Tamm, I. et al. The Lancet. Aug. 2001, 358: 489-497.*

Lepor et al, "Effect of Terazosin on Prostatism in Men With Normal and Abnormal Peak Urinary Flow Rates", Urology 49:476-480 (1997).

Broten et al, "Alpha-1 Adrenoceptor Blockade Inhibits Detrusor Instability in Rats With Bladder Outlet Obstruction", Monday AM, Adrenergic Pharmacology (2583-2588), FASEB J. 12:A445 (1998)—Abstract No. 2584.

Hampel, C, "Changes in α1 Adrenergic Receptor (AR) Subtype Gene Expression During Bladder Outlet Obstruction of Rats", The American Urological Association, Inc.® 95$^{th}$ Annual Meeting, Draft Preview of Abstract #351666, Wednesday, Nov. 10, 1999.

Beduschi et al, "Alpha-Blockade Therapy for Benign Prostatic Hyperplasia: From a Nonselective to a More Selective Alpha$_{1A}$-Adrenergic Antagonist", Urology 51:861-872 (1998).

Schulman et al, "Tamsulosin, the First Prostate-Selective $\alpha_{1A}$-Adrenoceptor[1] Antagonist", Eur. Urol. 29:145-154 (1996).

Kawabe et al, "Use of an $\alpha_1$-Blocker, YM-12617, in Micturition Difficulty", Urol. Int. 42:280-284(1987).

Walden et al, "Localization of mRNA and Receptor Binding Sites for the $\alpha_{1a}$-Adrenoceptor Subtype in the Rat, Monkey and Human Urinary Bladder and Prostate", The Journal of Urology 157:1032-1038 (1997).

Stafford Smith et al, α1-Adrenergic receptors in human spinal cord: specific localized expression of mRNA encoding α1-adrenergic receptor subtypes at four distinct levels, Molecular Brain Research 63:254-261 (1999).

Ferguson and Christopher, "Urinary bladder function and drug development", TIPS 17:161-165 (1996).

Reuther and Aagaard, "α-Adrenergic Blockade in the Diagnosis of Detrusor Instability Secondary to Infravesical Obstruction", Urol. Int. 39:312-313 (1984).

Hieble et al, International Union of Pharmacology X. Recommendation for Nomenclature of $\alpha_1$-Adrenoceptors: Consensus Update, Pharmaceutical Reviews 47(2):267-270 (1995).

Lepor, H., "Prostate Selectivity of Alpha-Blockers: From Receptor Biology to Clinical Medicine", Eur. Urol. 29(Suppl 1):12-16 (1996).

Graham et al, α1-Adrenergic Receptor Subtypes Molecular Structure, Function, and Signaling, Circ. Res. 78:737-749 (1996).

Schwinn et al, "Cloning and Pharmacological Characterization of Human *Alpha*-1 Adrenergic Receptors: Sequence Corrections and Direct Comparison with Other Species Homologues", The Journal of Pharmacological and Experimental Therapeutics, 272(1):134-142 (1995).

Price et al, "Expression of $_{\alpha 1}$-Adrenergic Receptor Subtype mRNA in Rat Tissues and Human SK-N-MC Neuronal Cells: Implications for $_{\alpha 1}$-Adrenergic Receptor Subtype Classification", Molecular Pharmacology 46:221-226 (1994).

Price et al, "Localization of mRNA for Three Distinct α1-Adrenergic Receptor Subtypes in Human Tissues: Implications for Human α-Adrenergic Physiology", Molecular Pharmacology 45:171-175 (1993).

Berkowitz et al, "Localization of Messenger RNA for Three Distinct α2-Adrenergic Receptor Subtypes in Human Tissues", Anesthesiology 81(5):1235-1244 (1994).

Berkowitz et al, "Distribution of β3-adrenoceptor mRNA in human tissues", European Journal of Pharmacology, Molecular Pharmacology Section 289:223-228 (1995).

Price et al, "Identification, Quantification, and Localization of mRNA for Three Distinct Alpha$_1$ Adrenergic Receptor Subtypes in Human Prostate", The Journal of Urology 150:546-551 (1993).

Maruyama et al, "Discrimination of $\alpha_1$-Adrenoceptor Subtypes in Rat Aorta and Prostate", Pharmacology 57:88-95 (1998).

Faure et al, "Identification of α1-Adrenoceptor Subtypes Present in the Human Prostate", Life Sciences 54(21):1595-1605 (1994).

Forray et al, "The α1-Adrenergic Receptor that Mediates Smooth Muscle Contraction in Human Prostate Has the Pharmacological Properties of the Cloned Human $\alpha_{1c}$ Subtype", Molecular Pharmacology 45:703-708 (1994).

Marshall et al, "Noradrenaline contractions of human prostate mediated by $\alpha_{1A}$-($\alpha_{1c}$-) adrenoceptor subtype", British Journal of Pharmacology 115:781-786 (1995).

Ford et al, "Pharmacological pleiotropism of the human recombinant α1A-adrenoceptor: implications for α1-adrenoceptor classification", British Journal of Pharmacology 121:1127-1135 (1997).

Ford et al, "RS-17053 (*N*-[2-(2-Cyclopropylmethoxyphenoxy)ethyl]-5-chloro-α, α-dimethyl-1*H*-indole-3-ethanamine hydrochloride), a Selective $\alpha_{1A}$-Adrenoceptor Antagonist, Displays Low Affinity for Functional $\alpha_1$-Adrenoceptorss in Human Prostate: Implications for Adrenoceptor Classification", Molecular Pharmacology 49:209-215 (1996).

Ford et al, "The putative αIL receptor (AR): a distinct pharmacological state of the alpha-1a-adrenoceptor", Br. J. Pharmacol. 118(Proc Suppl July):29P. English-Abstract, No. OM-96388.

Ford et al, "Pharmacological pleiotropism of the human recombinant alpha(1A)-adrenoceptor: implications for alpha1-adrenoceptor classification", Br. J. Pharmacol. 121(6):1127-1135 (1997) English-Abstract, No. OM-97188.

Testa et al, "Functional Antagonistic Activity of Rec 15/2739, a Novel *Alpha*-1 Antagonist Selective for the Lower Urinary Tract, on Noradrenaline-Induced Contraction of Human Prostate and Mesenteric Artery", The Journal of Pharmacology and Experimental Therapeutics 277:1237-1246(1996).

Maruyama et al, "Two Distinct α1-Adrenoceptor Subtypes in the Human Prostate: Assessment by Radioligand Binding Assay Using $^3$H-Prazosin", Gen. Pharmac. 27(8):1377-1381 (1996).

Yamagishi et al, "Effect of KMD-3213, an $α_{1a}$-adrenoceptor-selective antagonist, on the contractions of rabbit prostate and rabbit and rat aorta", European Journal of Pharmacology 315:73-79 (1996).

Mátyus and Horváth, "α-Adrenergic Approach in the Medical Management of Benign Prostatic Hyperplasia", Medicinal Research Reviews 17(6):523-535 (1997).

Chapple, C.R., "α-adrenergic blocking drugs in bladder outflow obstruction: what potential has α1-adrenoceptor selectivity?", British Journal of Urology 76 (Suppl 1):47-55 (1995).

Lepor et al, "The Impact of Medical Therapy on Bother Due to Symptoms Quality of Live and Global Outcome, and Factors Predicting Response", The Journal of Urology 160:1358-1367 (1998).

Andersen et al, "Prostatism", Scand. J. Urol. Nephrol. 13:229-236 (1979).

Chappel and Smith, "The pathophysiological changes in the bladder obstructed by benign prostatic hyperplasia", British Journal of Urology 73:117-123 (1994).

Christensen and Bruskewitz, "Clinical Manifestations of Benign Prostatic Hyperplasia and INidications for Therapeutic Intervention", Urologic Clinics of North America 17(3):509-516 (1990).

Steers et al, "Calcium channel antagonists preven urinary bladder growth and neuroplasticity following mechanical stress", Am. J. Physiol. 266 (Regulatory Integrative Comp. Physiol. 35):R20-R26 (1994).

Steers and De Groat, "Effect of Bladder Outlet Obstruction on Micturition Reflex Pathways in the Rat", The Journal of Urology 140:864-871 (1988).

Abrams, P., "Benign prostatic hyperplasia Poorly correlated with symptoms", BMJ 307:201 (1993).

Malloy et al, "α1-Adrenergic Receptor Subtypes in Human Detrusor", The Journal of Urology 160:937-943 (1998).

Witjes et al, "Urodynamic and Clinical Effects of Terazosin Therapy in Symptomatic Patients With and Without Bladder Outlet Obstruction: A Stratified Analysis", Urology 49:197-206 (1997).

Kirby, "Terazosin in benign prostatic hyperplasia: effects on blood pressure in normotensive and hypertensive men", British Journal of Urology 82:373-379 (1998).

Schmidbauer and Madersbacher, "[Current pharmacological treatment of benign prostatic hyperplasia]", Wien Med Wochenschr. 146(8):161-164 (1996), German-Abstract, No. OM-96357.

Roehrborn, C.G., "Rationale for the inclusion of alpha-adrenergic blockade in benign prostatic hyperplasia treatment guidelines", Eur. Urol. 29(Suppl 1):40-48 (1996), English-Abstract, No. OM-96120.

Hieble and Ruffolo, "The use of alpha-adrenoceptor antagonists in the pharmacological management of benign prostatic hypertrophy: an overview", Pharmacol. Res. 33(3):145-160 (1996), English-Abstract, No. OM-96277.

Kirby and Pool, "Alpha adrenoceptor blockade n the treatment of benign prostatic hyperplasia: past, present and future", Br. J. Urol. 80(4):521-532 (1997, English-Abstract, No. OM-97170.

Narayan and Tewari, "Overview of α-blocker therapy for benign prostatic hyperplasia", Urology 51(4 Suppl A):38-45 (1998)—Abstract, No. OM-98029.

Lepor et al, "A Randomized, Placebo-Controlled Multicenter Study of the Efficacy and Safety of the Terazosin in the Treatment of Benign Prostatic Hyperplasia", The Journal of Urology 148:1467-1474 (1992).

Buzelin et al, "Comparison of tamsulosin with alfuzosin in the treatment of patients with lower urinary tract symptoms suggestive of bladder outlet obstruction (symptomatic benign prostatic hyperplasia)", British Journal of Urology 80:597-605 (1997).

Caine, Marco, "Alpha-Adregeneric Blockers for the Treatment of Benign Prostatic Hyperplasia", Urologic Clinics of North America 17(3):641-649 (1990).

Serels and Stein, "Prospective Study Comparing Hyoscyamine, Doxazosin, and Combination Therapy for the Treatment of Urgency and Frequency in Women", Neurourology and Urodynamics 17:31-36 (1998).

Hieble and Ruffolo, Jr., "Recent advances in the identification of α1-and α2-adrenoceptor subtypes: therapeutic implications", Exp. Opin. Invest. Drugs 6(4):367-387 (1997).

Testa et al, "REC 15/2739, A New $α_1$-Antagonist Selective for the Lower Urinary Tract: In Vivo Studies", Abstracts, pp. 471-472 Abstract No. 84A.

Testa et al, "REC 15/2739, A New $α_1$-Antagonist Selective for the Lower Urinary Tract: In Vitro Studies", Abstracts, pp. 473-474 Abstract No. 84B.

Leonardi et al, "Pharmacological characterization of the uroselective alpha-1 antagonist REC 15/2739 (SB 216469): role of the alpha IL adrenoceptor in tissue selectivity, part I.", J. Pharmacol Exp. Ther. 281(3):1272-1283 (1997), English-Abstract, No. OM-97189.

Richardson et al, "Pharmacology of Tamsulosin: Saturation-Binding Isotherms and Competition Analysis Using Cloned $α_1$-Adrenergic Receptors Subtypes", The Prostate 33:55-59 (1997).

Noble et al, "The effects of tamsulosin, a high affinity antagonist at functional $α_{1A}$- and $α_{1D}$-adrenoceptor subtypes", British Journal of Pharmacology 120:231-238 (1997).

Abrams et al, "Tamsulosin, a Selective α1c-Adrenoceptor Antagnoist: A Randomized, Controlled Trial in Patients with Benign Prostatic 'Obstruction' (Symptomatic BPH)", Brit. J. Urol. 76:325-336 (1995)—Abstract, pp. 304-305.

Kurita et al, "Transition Zone Ratio and Prostate-Specific Antigen Density: The Index of Response of Benign Prostatic Hypertrophy to an Alpha Blocker", Int. J. Urol. 3:361-366 (1996).

Chapple et al, "Tamsulosin, the First Prostate-Selective $α_{1A}$-Adrenoceptor1 Antagonist", Eur. Urol. 29:155-167 (1996).

Barry et al, "Filling and Voiding Subscores of the AUA Symptom Index in a Trial of Tamsulosin for Benign Prostatic Hyperplasia (BPH)", The Journal of Urology 157(4):137, Supplement—Abstract No. 536.

Schulman et al, "Tamsulosin 0.4 Mg Once Daily: 2-Year Follow-Up Efficacy & Safety in 516 Symptomatic BPH Patients", The Journal of Urology 157(4):137, Supplement—Abstract No. 535.

Lepor and the Tamsulosin Investigator Group, "Tamsulosin, Long-Term, Open-Label, Extension Study to Evaluate Therapeutic Response and Safety", The Journal of Urology 157(4):331, Supplement—Abstract No. 1293.

Herbert Lepor for the Tamsulosin Investigator Group, "Long-Term Evaluation of Tamsulosin in Benign Prostatic Hyperplasia: Placebo-Controlled, Double-Blind Extension of Phase III Trial", Urology 51:901-906 (1998).

Kobayashi et al, "Is the effect of alpha 1a-selective blocker on voiding pressure durable in patients with benign prostatic obstruction? Longitudinal assessment by pressure flow study", Br. J. Urol 80(Suppl 2):193 (abs 754), English-Abstract, No. OM-97067.

Schulman et al, "Tamsulosin 0.4 Mg Once Daily: 2-Year Follow-Up Efficacy & Safety in 516 Symptomatic BPH Patients", British Journal of Urology 80(Suppl 2):194—Abstract No. 755.

"New Drug Approvals, Dosage Forms, and Other Product Announcements", Formulary 32:659-660(1997).

Lepor, H. for the Tamsulosin Investigator Group, "Phase III multicenter placebo-controlled study of tamsulosin in benign prostatic hyperplasia", Urology 51:892-900(1998).

Abrams et al, "A dose-ranging study of the efficacy and safety of tamsulosin, the first prostate-selective α1A-adrenoceptor antagonist, in patients with benign prostatic obstruction (symptomatic benign prostatic hyperplasia)", British Journal of Urology 80:587-596(1997.

Harada et al, "Comparison of the antagonistic activity of tamsulosin and doxazosin at vascular alpha1-adrenoceptors in humans", Naunyn Schmiedegerg's Arch Pharmacol. 354(5):557-561 (1996), English-Abstract, No. OM-96271.

Chapple et al, "Tamsulosin 0.4 mg once daily: tolerability in older and younger patients with lower urinary tract symptoms suggestive of benign prostatic obstruction (symptomatic BPH)", Eur. Urol 32(4):462-470 (1997), English-Abstract, No. OM-97173.

Lee and Lee, "Clinical comparison of selective and non-selective $\alpha_{1A}$-adrenoreceptor antagonists in benign prostatic hyperplasia: studies on tamsulosin in a fixed dose and terazosin in increasing doses", British Journal of Urology 80:606-611 (1997).

Rudner et al, "Subtype Specific Regulation of Human Vascular $\alpha_1$-Adrenergic Receptors by Vessel Bed and Age", Circulation 100(23):2336-43 (1999).

Andersson et al, "Prostatic $\alpha_1$-Adrenoceptors and Uroselectivity", The Prostate 30:202-215 (1997).

Docherty and O'Rourke, "The α-Adrenoceptor-Mediated Actions of Chloroethylclonidine", Gen. Pharmac. 28(2):197-201 (1997).

Michel and Rump, "α-Adrenergic regulation of human renal function", Fundam Clin Pharmacol 10:493-503 (1996).

Docherty, "Subtypes of functional $\alpha_1$- and $\alpha_2$-adrenoceptors", European Journal of Pharmacology 361:1-15 (1998).

Graham et al, "$\alpha_1$-Adrenergic Receptor Subtypes: Molecular Structure, Function, and Signaling", Circ Res. 78:737-749 (1996).

Anderson, W. French, "Human gene therapy", Nature 392:25-30 (1998).

Branch, Andrea D., "A good antisense molecule is hard to find", TIBS 23:45-50 (1998).

Agrawal, Sudhir, "Antisense oligonucleotides: towards clinical trials", TIBTECH 14:376-387 (1996).

Gewirtz et al, "Facilitating oligonucleotide delivery: Helping antisense deliver on its promise", Proc. Natl. Acad. Sci. USA 93:3161-3163 (1996).

Benedetti et al, "α1-Adrenoceptor Subtype Selectivity: Molecular Modelling and Theoretical Quantitative Structure-Affinity Relationship", Bioorganic & Medicinal Chemistry 5(5):809-816 (1997).

Goetz et al, "BMY 7378 is a selective antagonist of the D subtype of alpha 1-adrenoreceptors", Eur. J. Pharmacol. 272(2-3):R5-6 (1995)—Abstract.

Piascik et al, "Identification of the mRNA for the novel alpha 1D-adrenoceptor and two other alpha 1-adrenoceptors in vascular smooth muscle", Mol. Pharmacol. 46(1):30-40(1994)—Abstract.

Goetz et al, "BMY 7378 is a selective antagonist of the D subtype of alpha 1-adrenoreceptors", Eur. J. Pharmacol. 272(2-3):R5-6 (1995).

Piascik et al, "Identification of the mRNA for the novel alpha 1D-adrenoceptor and two other alpha 1-adrenoceptors in vascular smooth muscle", Mol. Pharmacol. 46(1):30-40(1994).

* cited by examiner

METHOD OF TREATING BLADDER AND LOWER URINARY TRACT SYNDROMES

This application is a continuation of application Ser. No. 09/306,013, filed May 6, 1999, now abandoned, the entire content of which is hereby incorporated by reference in this application, and application Ser. No. 09/306,031 claims priority from U.S. Provisional Application Ser. No. 60/084,479, filed May 6, 1998, the entire contents of that application being incorporated herein by reference

TECHNICAL FIELD

The present invention relates to bladder and lower urinary tract syndromes, particularly, irritative symptoms, and to a method of treating same using $\alpha_{1d}$-adrenergic receptor ($\alpha_{1d}$AR) antagonists. The invention further relates to a method of screening compounds for their ability to serve as $\alpha_{1d}$AR antagonists.

BACKGROUND

Lower urinary tract symptoms (LUTS) resulting from bladder outlet obstruction (BOO) remains one of the most commonly encountered disorders in urology, and can be secondary to fixed anatomical and/or functional causes (Steers et al, Voiding dysfunction: diagnosis, classification. and management, in Adult and Pediatric Urology; Third Edition, J. Y. Gillenwater. et al., Editors. 1996, Mosby-Year Book, Inc.: St. Louis. p. 1220-1325.). Causes of BOO include prostatic enlargement (benign or malignant), bladder neck contracture, urethral stricture, and meatal stricture (Steers et al, Voiding dysfunction: diagnosis, classification, and management, in Adult and Pediatric Urology; Third Edition, J. Y. Gillenwater, et al., Editors. 1996, Mosby-Year Book, Inc.: St. Louis. p. 1220-1325.). Symptoms associated with BOO typically fall into obstructive or irritative categories; obstructive symptoms include hesitancy, poor stream, prolonged urination, and feelings of incomplete emptying, while irritative symptoms consist of frequency, urgency. nocturia. and unstable bladder contractions. The bladder is functionally and anatomically divided into the detrusor (body and ventral base) and trigone (dorsal portion of base extending between the ureteral orifices and the bladder neck) (Zderic et al. Voiding function: relevant anatomy, physiology. pharmacology, and molecular aspects, in Adult and Pediatric Urology; Third Edition, J. Y. Gillenwater, et al., Editors. 1996, Mosby-Year Book, Inc.: St. Louis. p. 1159-1219), with distinct histology, histochemistry, and pharmacology. In contrast, the prostate and trigone have similar vascular supply, innervation, and receptor expression (Gosling et al. Detrusor morphology in relation to bladder outflow obstruction and instability, in Benign Prostatic Hypertrophy. F. Hinman, Editor. 1983, Springer-Verlag: Berlin. p. 666-71).

The physiology of LUTS secondary to benign prostatic hypertrophy (BPH) has two components: (1) a static component related to the increase in prostatic cellular mass and (2) a dynamic component related to variations in prostatic smooth muscle tone (Caine et al, Brit. J. Urol. 47:193-202 (1975)). Histologically BPH is characterized by glandular (epithelial) and stromal (fibromuscular) hyperplasia, with the latter being the dominant factor in the pathogenesis of clinically significant BPH (Shapiro et al, J. Urol. 147:1293-1297 (1992)). Therefore much attention has focused on the role of the sympathetic nervous system and $\alpha_1$-adrenergic receptors ($\alpha_1$ARs) in the dynamic component of BOO, leading to clinical studies of $\alpha_1$AR antagonists as agents to relieve outlet obstruction. These studies have found that $\alpha_1$AR antagonists relax prostatic smooth muscle, relieving obstructive symptoms (Chapple, Brit. J. Urol. 1:47-55 (1995), Caine, Urol. Clin. N. Am. 17:641-649 (1990), Kawabe and Niijima, Urol. Int. 42:280-284 (1987), Lepor et al, J. Urol. 148:1467-1474 (1992), Reuther and Aagaard, Urol. Int. 39:312-313 (1984), Matyus and Horvath. Med. Res. Rev. 17:523-535 (1997)). In addition, $\alpha_1$AR antagonists have been found to relieve the irritative bladder symptoms in men (most often associated with BPH) and women (Matyus and Horvath, Med. Res. Rev. 17:523-535 (1997), Serels and Stein, Neurourol. Urodyn. 17:31-36 (1998)). While it is logical to assume that elimination of BOO would relieve irritative symptoms, a number of recent studies suggest that the relationship between bladder irritability and outlet obstruction is not straightforward (Caine, Urol. Clin. N. Am. 17:641-649 (1990), Chapple and Smith, Brit. J. Urol. 73:117-123 (1994), Steers and De, J. Urol. 140:864-71 (1988), Steers et al, Am. J. Physiol. 266: R20 (1994)).

$\alpha_1$ARs are members of the larger family of G protein-coupled adrenergic receptors which mediate actions of the endogenous catecholamines norepinephrine (NE) and epinephrine, resulting in smooth muscle contraction. cDNAs encoding three distinct $\alpha_1$AR subtypes ($\alpha_{1a}$, $\alpha_{1b}$, $\alpha_{1d}$) have been cloned, expressed in cells, and resultant protein characterized pharmacologically (Schwinn et al, J. Pharmacol. Exper. Ther. 272:134-142 (1995), Hieble et al, Pharmacol. Rev. 47:267-70 (1995)). $\alpha_{1a}$ARs predominate in prostate and bladder trigone (Price et al, J. Urol. 150:546-551 (1993)), and have been shown to be functionally important in mediating prostate smooth muscle contraction (Forray et al, Mol. Pharmacol. 45:703-708 (1994), Lepor et al., J. Pharmacol. Exper. Ther. 270:722-727 (1994)). In addition to the three cloned $\alpha_1$AR subtypes which have high affinity for the antagonist prazosin, a fourth type of $\alpha_1$AR with low affinity for prazosin ($\alpha_{1L}$) has been postulated (Muramatsu et al, Brit. J. Urol. 74:572-578 (1994)). In spite of initial evidence suggesting a role for the $\alpha_{1L}$AR in human prostate smooth muscle contraction (Ford et al, Mol. Pharmacol. 49:209-215 (1996)), more recent data suggests RS17053 (the compound used in these studies) detects a low affinity state of the $\alpha_{1a}$AR in tissues rather than a distinct $\alpha_{1L}$AR (Ford et al. Br. J. Pharmacol. 121:1127-1135 (1997)). Since non-selective $\alpha_1$AR antagonists currently used to treat BPH have undesirable side-effects including light headedness, dizziness, and asthenia (Carruthers. Drug Safety 11:12-20 (1994)), many investigators have suggested that $\alpha_{1a}$AR subtype selective antagonists might be beneficial in improving BPH-related symptoms via relieving BOO (Matyus and Horvath, Med. Res. Rev. 17:523-535 (1997), Hieble and Ruffolo, Jr., Exp. Opin. Invest. Drugs 6:367-387 (1997)). However, this approach does not take into account that irritative symptoms may persist in spite of relief of outlet obstruction (Hieble and Ruffolo, Jr., Exp. Opin. Invest. Drugs 6:367-387 (1997)).

Very little information exists regarding the role of $\alpha_1$ARs in human detrusor. One of the few studies addressing this issue suggests human bladder (dome) contains only $\alpha_{1a}$ARs (Walden et al. J. Urol. 157:1032-1038 (1997)). However, since irritative bladder symptoms persist in some patients despite relief of BOO, nonselective $\alpha_1$AR antagonists may relieve the irritative effects of BPH through direct effects on bladder detrusor or other sites involved in micturation. The present invention results from the realization that human detrusor expresses two $\alpha_1$AR subtypes ($\alpha_{1d}$>$\alpha_{1a}$). This realization makes possible the identification of $\alpha_1$AR subtype selective antagonists that can be used to treat irritative symptoms.

SUMMARY OF THE INVENTION

The present invention relates generally to bladder and lower urinary tract syndromes and, more particularly, to a method of identifying $\alpha_{1d}$AR antagonists that can be used to treat irritative symptoms. The invention also relates to a method of treating irritative symptoms using such agents.

Objects and advantages of the invention will be apparent from the detailed description that follows.

DETAILED DESCRIPTION OF THE INVENTION

Figure 1:
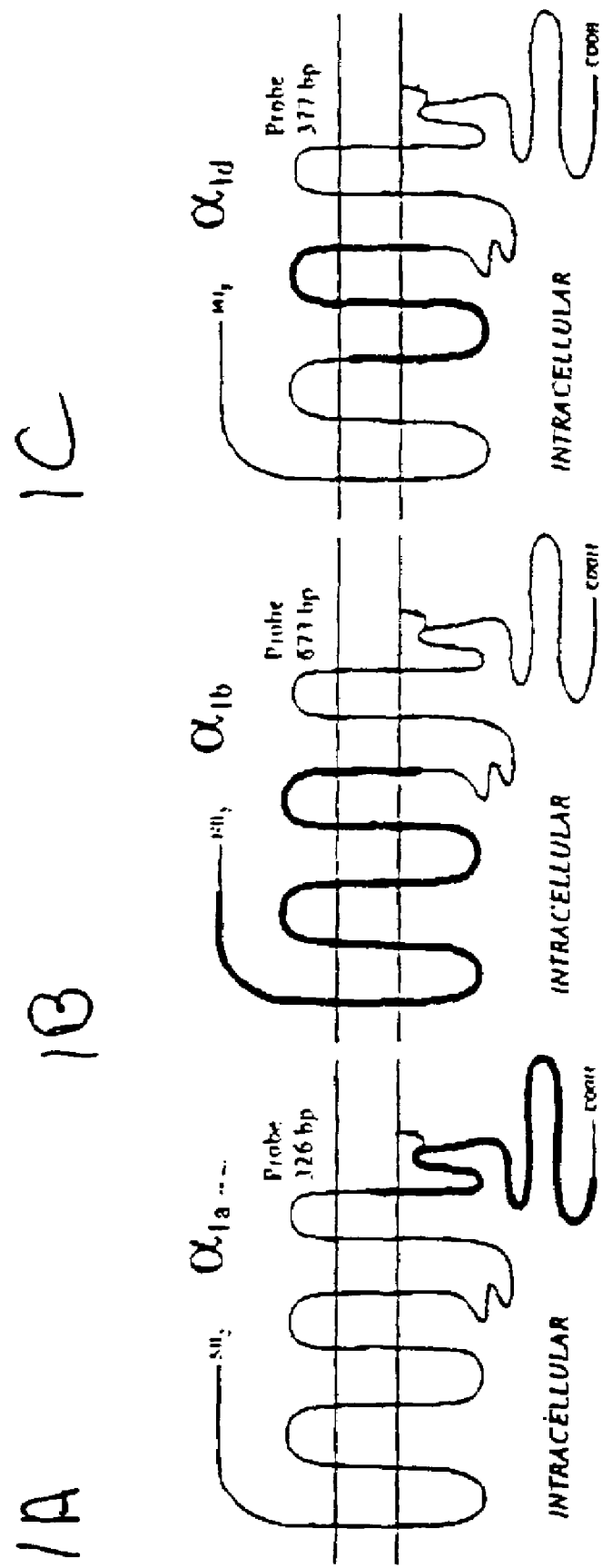
FIGS. 1A-1C. Schematic of the location of $\alpha_1$AR subtype probes. Highlighted in bold are regions of $\alpha_{1a}$ (FIG. 1A), $\alpha_{1b}$ (FIG. 1B), and $\alpha_{1d}$ (FIG. 1C) ARs encoded by probes used in RNase protection assays.

The present invention is based on the recognition of $\alpha_{1d}$AR as the $\alpha_1$AR subtype responsible for irritative symptoms associated with bladder and lower urinary tract diseases. The invention provides, in one embodiment. a method of selecting $\alpha_{1d}$AR antagonists and, in a further embodiment, a method of treating irritative symptoms using $\alpha_{1d}$AR antagonists. (The nomenclature used herein is the new nomenclature provided in Hieble et al, Phar. Rev. 97:267 (1995)).

The method of treatment to which the invention relates comprises administering to a patient suffering irritative symptoms an amount of an $\alpha_{1d}$AR antagonist sufficient to relieve such symptoms. In accordance with the invention, irritative symptoms include excessive frequency of urination, urgency of urination, nocturia and unstable bladder contractions. Patients amenable to treatment include men and women, children and adults. In males, a preferred antagonist is both an $\alpha_{1a}$AR and an $\alpha_{1d}$AR antagonist. In females, preferred antagonists are $\alpha_{1d}$AR specific antagonists. The amount of the antagonist to be administered and the treatment regimen will vary with the antagonist, the patient and the effect sought. Optimum doses and regimens, however, can be readily determined by one skilled in the relevant art.

The present invention also relates to a method of screening compounds for their ability to bind primarily to $\alpha_{1d}$AR and thereby to function, potentially. as $\alpha_{1d}$AR antagonists Preferred $\alpha_{1d}$AR selective antagonists show at least a two fold selectivity for $\alpha_{1d}$AR relative to $\alpha_{1a}$AR or $\alpha_{1b}$AR. Binding assays of this embodiment invention include cell-free assays in which $\alpha_{1d}$AR. or portion thereof (e.g. relevant transmembrane portion—see, generally. Hwa et al. J. Biol. Chem. 271: 7956 (1996)). is incubated with a test compound (proteinaceous or non-proteinaceous) which. advantageously, bears a detectable label (e.g., a radioactive or fluorescent label). Preparations of membranes that bear $\alpha_{1d}$AR can be used in this assay. including commercially available preparations (e.g. the NEN multireceptor kit (NET 1034)). Following incubation. the $\alpha_{1d}$AR, or portion thereof. free or bound to test compound. can be separated from unbound test compound using any of a variety of techniques (for example, the $\alpha_{1d}$AR (or portion thereof) (e.g., associated with a membrane) can be bound to a solid support (e.g., a plate or a column) and washed free of unbound test compound). The amount of test compound bound to or $\alpha_{1d}$AR. portion thereof is then determined using a technique appropriate for detecting the label used (e.g., liquid scintillation counting in the case of a radiolabelled test compound). (See Schwinn et al, J. Pharm. Exp. Ther. 272:134 (1995).)

Binding assays of this embodiment can also take the form of cell-free competition binding assays. Such assays can be conducted as described in the Examples that follow (see particularly Example 2 (the test compound being substituted for BMY7378)—see also Schwinn et al, J. Pharm. Exp. Ther. 272:134 (1995)). Alternatively, $\alpha_{1d}$AR, or portion thereof, can be incubated with a compound known to interact, specifically. with $\alpha_{1d}$AR (e.g., BMY7378), which compound, advantageously, bears a detectable label (e.g., a radioactive or fluorescent label). A test compound (proteinaceous or non-proteinaceous) is added to the reaction and assayed for its ability to compete with the known (labeled) compound for binding to $\alpha_{1d}$AR, or portion thereof. Free known (labeled) compound can be separated from bound known compound, and the amount of bound known compound determined to assess the ability of the test compound to compete. This assay can be formatted so as to facilitate screening of large numbers of test compounds by linking the $\alpha_{1d}$AR. or portion thereof or, to a solid support so that it can be readily washed free of unbound reactants.

$\alpha_{1d}$AR. or portion thereof. suitable for use in the cell-free assays described above can be isolated from natural sources (e.g., as membrane preparations derived from bladder, e.g., human bladder) or prepared recombinantly or chemically. The $\alpha_{1d}$AR. or portion thereof, or can be prepared as a fusion protein using, for example, known recombinant techniques. Preferred fusion proteins include a HIS tag, a FLAG tag, a GFP tag or other tag (moiety) suitable for use in colorimetric assays. Typically, the non-$\alpha_{1d}$AR moiety is present in the fusion protein N-terminal to the $\alpha_{1d}$AR, or portion thereof domain, but it can also be C-terminal.

As indicated above, the $\alpha_{1d}$AR, or portion thereof, can be present linked to a solid support, including a plastic or glass plate or bead, a chromatographic resin, a filter or a membrane. Methods of attachment of proteins, or membranes containing same. to such supports are well known in the art.

The binding assays of the invention also include cell-based assays in which $\alpha_{1d}AR$, or portion thereof, is associated with the cell membrane of an intact cell. Cells suitable for use in such assays include cells that naturally express $\alpha_{1d}AR$ and cells that have been engineered to express, advantageously, over express, $\alpha_{1d}AR$ (or portion thereof). Advantageously, cells expressing human $\alpha_{1d}AR$ are used. Suitable cells are preferably eucaryotic, including mammalian (human and nonhuman) cells. insect cells and yeast cells.

Cells can be engineered to express $\alpha_{1d}AR$ (advantageously. human $\alpha_{1d}AR$. or portion thereof) by introducing into a selected host (e.g. a eucaryotic host) an expression construct comprising a sequence encoding $\alpha_{1d}AR$, or portion thereof, operably linked to a promoter. A variety of vectors and promoters can be used. (See Schwinn et al, J. Pharm. Exp. Ther. 272:134 (1995).) Introduction of the construct into the host can be effected using any of a variety of standard transfection/transformation protocols (see Molecular Biology, A Laboratory Manual, second edition. J. Sambrook, E. F. Fritsch and T. Maniatis, Cold Spring Harbor Press, 1989). Cells thus produced can be cultured using established culture techniques suitable for the involved host. Culture conditions can be optimized to ensure expression of the $\alpha_{1d}AR$ (or portion thereof) encoding sequence.

While for the cell-based binding assays it is appropriate that the $\alpha_{1d}AR$ (or portion thereof) be associated with the cell membrane, for other purposes the expression product can be secreted into the culture medium or present in the cell cytoplasm.

The cell-based binding assays of the invention can be carried out essentially as described above with respect to the cell free assays. Advantageously. the cell used expresses predominantly the $\alpha_{1d}AR$ subtype. By way of example. the cell-based binding assay can be carried out by adding test compound (advantageously. bearing a detectable (e.g., radioactive or fluorescent) label), to medium in which the $\alpha_{1d}AR$ (or portion thereof) expressing cells are cultured, incubating the test compound with the cells under conditions favorable to binding and then removing unbound test compound and determining the amount of test compound associated with the cells.

As in the case of the cell-free assays, the cell-based assays can also take the form of competitive assays, as described above. For example. a compound known to bind $\alpha_{1d}AR$ (and preferably labelled with a detectable label) can be incubated with $\alpha_{1d}AR$ (or portion thereof) expressing cells in the presence and absence of test compound. The affinity of a test compound for $\alpha_{1d}AR$ can be assessed by determining the amount of known compound associated with the cells incubated in the presence of the test compound. as compared to the amount associated with the cells in the absence of the test compound.

A test compound identified in one or more of the above-described assays as being capable of binding to $\alpha_{1d}AR$ can. potentially. serve as an $\alpha_{1d}AR$ antagonist and therefore be suitable for use in the irritative symptom treatment method of the invention. To determine the specific effect of any particular test compound selected on the basis of its ability to bind $\alpha_{1d}AR$, various assays can be used including IP assays (see Schwinn et al, J. Pharm. Exp. Ther. 272:134 (1995)) and bladder (e.g. human bladder) smooth muscle contraction assays (Ford et al, Mol. Pharm. 49:209 (1996)). Compounds suitable for use in treating irritative symptoms will be associated with antagonistic (inhibitory) effects in the IP assay and contraction inhibitory effects in the contraction assay.

In another embodiment, the invention relates to compounds identified using the above-described assays as being $\alpha_{1d}AR$ antagonist. The compounds identified in accordance with the above assays can be formulated as pharmaceutical compositions. Such compositions comprise the compound and a pharmaceutically acceptable diluent or carrier. The compound can be present in dosage unit form (e.g., as a tablet or capsule) or as a solution, preferably sterile, particularly when administration by injection is anticipated. The dose and dosage regimen will vary, for example, with the patient. the compound and the effect sought. Optimum doses and regimens can be determined readily by one skilled in the art.

In another embodiment, the invention relates to antibodies specific for a $\alpha_{1d}AR$, and antigen binding fragments thereof. including $F(ab)_2$' or $F(ab)$ fragments. The antibodies can be monoclonal or polyclonal and can be prepared using standard techniques. The antibodies can be used in $\alpha_{1d}AR$ purification protocols or the antibodies can be formulated as pharmaceutical compositions and used therapeutically as $\alpha_{1d}AR$ antagonists.

In yet another embodiment, the present invention relates to a gene therapy approach to treating irritative symptoms. In this embodiment, oligonucleotides (constructs) are used that, upon administration, result in the production of a molecule that down regulates production of $\alpha_{1d}AR$. In a related embodiment, the present invention relates to $\alpha_{1d}AR$ antisense constructs and to a method of using same to treat irritative symptoms. Such constructs can be designed to target any of a variety of regions of the $\alpha_{1d}AR$ gene, including the encoding sequence (e.g., regions encoding the intracellular portion that interacts with G protein and participates in the signal transduction pathway) and the 5'-untranslated region.

Delivery of the above-described constructs can be effected using any of a variety of approaches, including installation into the bladder (e.g. via the uretha) and introduction into the cerebrospinal fluid. The constructs can also be administered systemically, in which case targeting can be effected using, for example, smooth muscle (e.g. bladder smooth muscle) specific promoters.

Effective vectors for use in the above-described gene therapy/antisense embodiments include viral vectors, such as retroviral vectors, adenoviral vectors and adenoassociated viral vectors. The constructs can also be present in association with a lipid, e.g. a liposome. (For details of antisense constructs and delivery systems, etc. see, for example, Wagner Nature 372:333 (1994).) The amount of construct to be administered will vary, for example, with the construct. the patient and the effect sought. One skilled in the relevant art can readily optimize the dose and treatment regimen.

In yet another embodiment, the invention relates to kits, for example. kits suitable for conducting assays described herein. Such kits can include $\alpha_{1d}AR$, or portion thereof, for example, bound to a solid support. The kit can include an $\alpha_{1d}AR$-encoding sequence, $\alpha_{1d}AR$ antisense construct or $\alpha_{1d}AR$-specific antibody. The kit can include any of the above components disposed within one or more container means. The kit can further include ancillary reagents (e.g., buffers) for use in the assays.

Certain aspects of the present invention are described in greater detail in the non-limiting Examples that follow.

EXAMPLES

The following experimental details are relevant to the specific Examples that follow.

Tissue preparation. Full-thickness human bladder detrusor was obtained as discarded "normal" tissue adjacent to tumor specimens (n=1 radical cystectomy, n=12 radical cystoprostatectomy for transitional cell carcinoma of the bladder) with appropriate institutional approval. Each sample was inspected by a pathologist and normal tissue confirmed. Detrusor smooth muscle was grossly teased from urothelial and serosal layers, snap frozen in liquid nitrogen within 30 minutes of excision, and stored at −70° C. for later use. Whole rat bladder was obtained from euthanized male Sprague-Dawley rats (Charles River Laboratories; Wilmington, Mass.) with institutional animal care committee approval. Rat tissue was harvested within two minutes of death, snap frozen in liquid nitrogen. and stored at −70° C. for later use.

Human detrusor and rat bladder membrane preparation. Human detrusor and rat whole bladder was minced over dry ice, and suspended in cold lysis buffer (5 mM Tris HCl and 5 mM EDTA, pH7.4) with protease inhibitors benzamidine (10 mg/ml), leupeptin (5 mg/ml), and soybean trypsin inhibitor (10 mg/ml) (Sigma Chemical Company; St. Louis, Mo.). A lysate was prepared with a Polytron PT 3000 (Brinklmann; Westbury, N.Y.) at 10,000 rpm for 10 seconds. After pelleting at 40,000×g for 15 minutes (Sorvall SM24 rotor), membranes were suspended in cold resuspension buffer (150 mN NaCl, 50 mN Tris HCl, 5 mM EDTA, pH7.4) with protease inhibitors. and kept on ice for immediate use (or stored at −70° C. for later use). Protein content was determined using the bicinchoninic assay (BCA) with bovine serum albumin (BSA) standards (Pierce; Rockford, Ill.).

Radioligand binding. All mRNA and protein studies described were performed using detrusor from each patient described above (n=13). In order to conserve sample, and yet fully characterize $a_1$ARs in human detrusor. additional full saturation binding isotherms were generated in human detrusor samples from a subset of patients (n=5) using a buffer consisting of 150 mM NaCl. 50 mN Tris HCl and 5 mM EDTA, pH7.4, with protease inhibitors. Each reaction was performed in triplicate. in a total volume of 0.25 ml. including diluted human detrusor membranes (50 to 100 mg protein) and the $\alpha_1$AR antagonist [$^{125}$I]HEAT (NEN Research Products-DuPont; Boston, Mass.) ranging in concentration from 2-900 pM; nonspecific binding was measured in the presence of 1 mM prazosin (Sigma). The reaction proceeded at 25° C. for 45 minutes. and was terminated with five-fold dilution of ice-cold 50 mM Tris HCl, pH7.4 buffer, followed by rapid filtration over GF/C filters using a Brandel harvester. Dried filters were then counted in a gamma counter. Specific binding was calculated by subtracting nonspecific binding from total binding. Saturation curves were fit with noniterative regression analysis using InPlot software (GraphPad; San Diego, Calif.). Total $\alpha_1$AR density was then determined in each detrusor sample as described above, using a saturating concentration of [$^{125}$I]HEAT (300 pM). Results are reported as mean±SEM to two significant figures.

To determine Ki values in human detrusor for $\alpha_1$AR subtype discriminating ligands, competition binding was performed in triplicate in a total volume of 0.25 ml using binding buffer (see saturation binding above). Human detrusor membranes (50 to 100 μg protein) were incubated with a $K_d$ concentration (120 pM) of the $\alpha_1$AR antagonist [$^{125}$I]HEAT, and increasing concentrations ($10^{-12}$ to $10^{-3}$M) of the nonradiolabeled $\alpha_{1d}$AR-selective ligand BMY7378 (Research Biochemicals International; Natick, Mass.). Reaction conditions were as described above. Curves were fit with noniterative regression analysis using InPlot software (GrapiPad).

Preparation of RNA. Total RNA was extracted from human detrusor or rat whole bladder samples using the RNazol method (Tel-Test, Inc.; Friendswood, Tex.). RNA was quantitated using a spectrophotometer at 260/280 nm, and aliquoted into 20 mg samples for immediate use.

Human $\alpha_1$AR cDNA constructs. The human $\alpha_{1a}$AR probe consists of a 0.326 kb (PvuII/HindIII) fragment in pGEM-4Z (Promega Corporation; Madison, Wis.), corresponding to nucleotides 958-1283 of the cloned human $\alpha_{1a}$AR cDNA (GenBank #L31774). The human $\alpha_{1b}$AR probe consists of a 0.673 kb (XhoI/BamHI) fragment in pGEM-4Z (Promega), corresponding to nucleotides 94-766 of the cloned human $\alpha_{1d}$AR cDNA (GenBank #L31773). The human $\alpha_{1d}$AR probe consists of a 0.377 kb (EcoRI/PstI) fragment, corresponding to nucleotides 520-896 of the cloned human $\alpha_{1d}$AR cDNA (GenBank #L31772). FIG. 1 shows the location of each $\alpha_1$AR subtype probe within a schematic of the encoded protein. The human cyclophilin probe consists of a 0.103 kb (KpnI/EcoRI) fragment in pTRI (Ambion, Inc.; Austin, Tex.), corresponding to nucleotides 38-140 of the cloned human cyclophilin gene (GenBank #X52856).

Labeling of RNA probes. Antisense single-stranded radiolabeled RNA probes were generated from linearized $\alpha_1$AR cDNA constructs using RNA polymerase T7 ($\alpha_{1a}$, cyclophilin) and SP6 ($\alpha_{1b}$, $\alpha_{1d}$) as described in the Promega Protocols and Applications Guide (Promega Corporation; Madison, Wis.). $\alpha_{1a}$AR and $\alpha_{1d}$AR cDNA constructs were linearized with EcoRI, and the $\alpha_{1b}$AR cDNA construct was linearized with HindIII. $^{32}$P-αUTP (NEN Research Products-DuPont) was incorporated into RNA probes at the time of probe synthesis. All probes were purified on a 5% polyacryalminde gel (300V for 1.5 hr); after exposure to film for 3 min, radiolabeled RNA probes were excised from the gel and passively eluted overnight into 400 μl of RPA II kit (Ambion) elution buffer at 37° C.

RNase protection assays. RNase protection assays were conducted as previously described (Zinn et al, Cell 34:865-879 (1983)) with a few modifications. In brief, total RNA samples (20 mg) were dissolved in 20 ml of hybridization buffer containing >20-fold excess of radiolabeled probe ($2 \times 10^5$ cpm/reaction for $\alpha_{1a}$, $\alpha_{1b}$, $\alpha_{1d}$, and $1 \times 10^5$ cpm/reaction for cyclophilin). and incubated overnight at 55° C. ($\alpha_{1a}$, $\alpha_{1b}$) and 65° C. ($\alpha_{1d}$, cyclophilin). To ensure specificity of the synthesized radiolabeled antisense human $\alpha_1$AR subtype selective probes, RNase protection assays were performed in tandom with total RNA extracted from rat-1 fibroblast cells stably expressing each cloned human $\alpha_1$AR subtype. As a negative control, RNase protection assays for each $\alpha_1$AR subtype selective probe were performed in tandom with yeast tRNA samples and other non-hybridizing $\alpha_1$AR subtypes. Antisense radiolabeled probe to the highly conserved region of the constitutively expressed human cyclophilin gene was also utilized as a control to ensure identical amounts of total RNA in each assay. The final gel was exposed to X-Omat AR film (Eastman Kodak Company: Rochester, N.Y.) for 24-72 hours.

$\alpha_1$AR mRNA quantitation in human detrusor smooth muscle from RNase protection assays. In order to quantitate relative $\alpha_1$AR subtype mRNA, each RNase protection assay final gel was exposed to Phosphorimager plates (Molecular Dynamics: Sunnyvale, Calif.) for 24 hours. Volume integration of specific protected radiolabeled bands for each mRNA resulting from hybridization products was corrected for background, normalized for cyclophilin signal, and expressed as arbitrary density units, using ImageQuant gel image-analysis software (Molecular Dynamics). $\alpha_1$AR probes contained the following number of UTP sites for $^{32}$P-αUTP incorporation: $\alpha_{1a}$ 88, $\alpha_{1b}$ 117, $\alpha_{1d}$ 51. Arbitrary density units were normalized to the lowest $^{32}$P-αUTP incorporating probe ($\alpha_{1d}$AR) and then expressed as a fraction (±SEM) of total $\alpha_1$AR mRNA signal strength.

Polymerase Chain Reaction (PCR). RT-PCR was used to confirm expression of human detrusor $\alpha_1$AR subtypes (to ensure low concentrations of a subtype were not missed in human bladder) and to compare $\alpha_1$AR subtype mRNA expression in rat whole bladder with previously published rat data (Walden et al, J. Urol. 157:1032-1038 (1997), Scofield et al, J. Pharmacol. Exper. Ther. 275:1035-1042 (1995)). Human and rat $\alpha_1$AR subtype primers were synthesized at Duke University Medical Center. Reverse transcription of 1 mg of DNase-treated human detrusor or rat bladder RNA was performed in triplicate in a 20 ml reaction mixture containing 5 mM MgCl$_2$, 1 mM each of dATP, dCTP, dGTP, and dTTP, 10 mM Tris HCl, 50 mM KCl, 2 ml DEPC treated water, 2.5 mM random hexamers, 1 unit of RNase inhibitor, and 2.5 units of MuLV Reverse Transcriptase (Perkin Elmer; Foster City. Calif.); simultaneous control samples not treated with reverse transcriptase were used to rule out amplification of genomic DNA. Reverse transcriptase reactions were run for 60 min at 42° C. 5 min at 95° C. and 10 min at 4° C. Each $\alpha_1$AR mRNA subtype was amplified by PCR in triplicate in a 100 ml reaction containing 50 mM KCl, 10 mM Tris HCl pH8.3, 2 mM MgCl$_2$, 200 mM each of dATP, dCTP. dGTP and dTTP, 15 pM of sense and antisense primer. 5% DMSO, and 2.5 units of AmpliTaq DNA polymerase (Perkin Elmer). PCR reactions were performed in a DeltaCycler II™ temperature cycler (ERICOMP; San Diego, Calif.). The following conditions were established for all three rat primer sets: one denaturation cycle for 3 minutes at 95° C., 35 cycles of 1 min at 95° C., 1 min annealing at 58° C. and a 1 min extension at 72° C. The following conditions were established for all three human primer sets: one denaturation cycle for 3 minutes at 95° C., 35 cycles of 1 min at 95° C. 1 min annealing at 60° C. for $\alpha_{1a}$ and $\alpha_{1b}$, and 68° C. for $\alpha_{1d}$, and a 1 min extension at 72° C. A final extension cycle was performed for 10 min at 72° C. Reaction mixtures were then cooled at 4° C. 10 ml of each PCR product was separated by gel electrophoresis in 0.8% agarose. Since PCR experiments were only confirmatory in nature by design, exact quantitation (requiring competitive PCR) was not performed. However, to ensure that any statement regarding relative mRNA levels is appropriate, it is important to note that conditions described above (e.g. different annealing temperatures) were chosen after extensive preliminary analysis with each primer set to ensure optimal amplification conditions with similar primer product efficiency. Equality of reverse transcription efficiency for products was checked using equal concentrations of starting control cDNA: these reactions also served as a positive control for use of correct primer sets. Thirty-five cycles of amplification was chosen since it is at the upper end of the linear amplification range for all six primer sets ($\alpha_1$AR mRNAs are rare at baseline in many human tissues and in our hands 40 cycles of amplification is where the curve becomes non-linear).

Example 1

Human Patient Population

Human detrusor smooth muscle was obtained from male (n=12) and female (n=1) patients. Patient age ranged from 56 to 76 years old (mean=59.6). Significant past medical history included tobacco abuse, coronary artery disease, hypertension controlled with $\alpha_1$AR or $\beta$AR antagonists (n=3), and a history of BOO (n=2) necessitating previous transurethral resection of prostate. Comparison of results from patients with hypertension and/or BOO (n=5) suggests medical history did not affect the results. A larger study would be required to make any definitive statement in this regard.

Example 2

$\alpha_1$AR Ligand Saturation Binding

Figure 2:
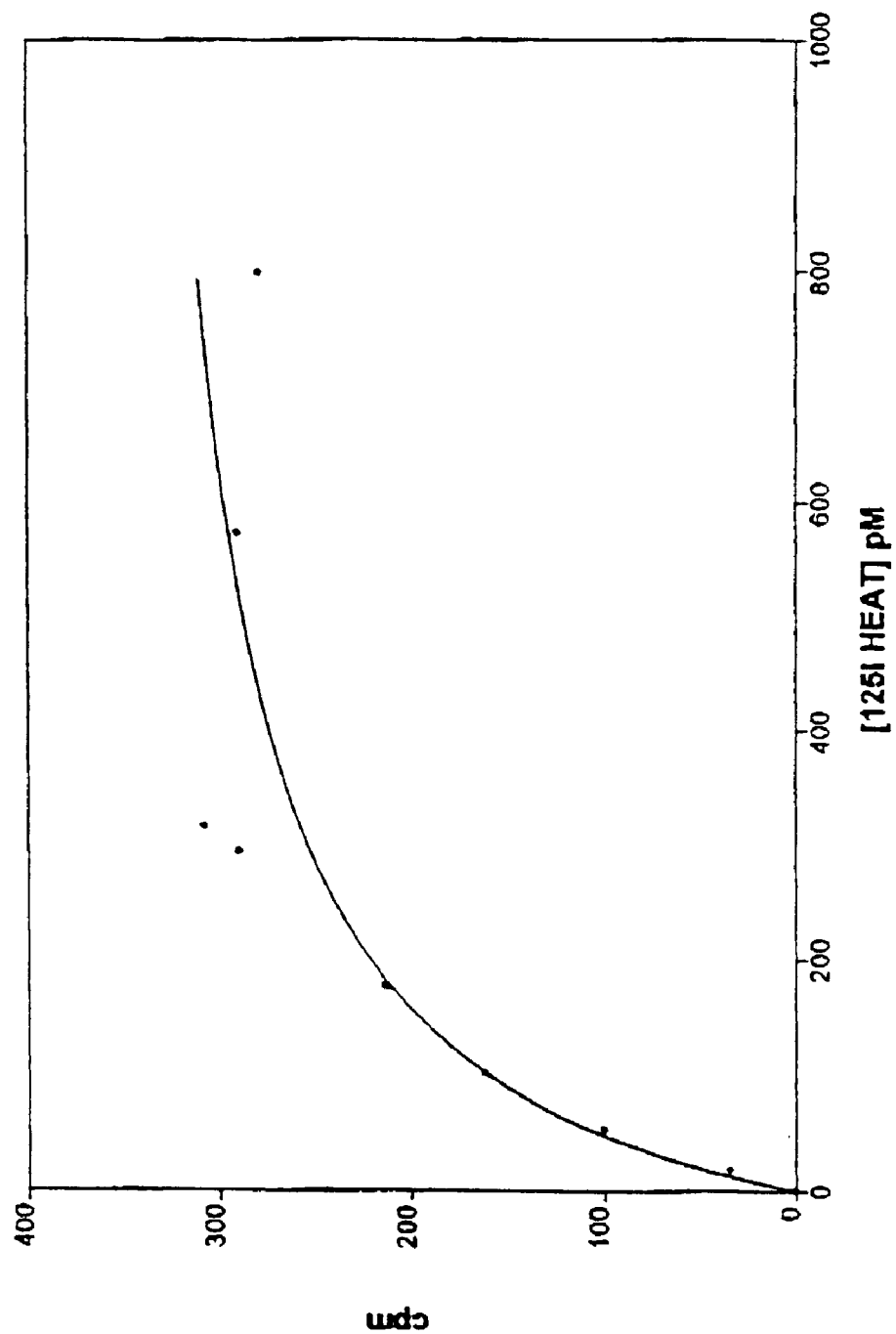
FIG. 2. Representative saturation binding isotherm generated using increasing concentrations of the $\alpha_1$AR radiolabeled antagonist [($^{125}$I)]HEAT in human detrusor membranes. Kd is 130=1.09 pM (n=5), similar to that reported for cells stably expressing each cloned human $\alpha_1$AR subtype (Schwinn et al, J Pharmacol. Exper. Ther. 272:134-142 (1995)—$\alpha_{1a/d}$AR of the reference refers to the $\alpha_{1d}$AR subtype described herein since the $\alpha_1$AR nomenclature used here is the IUPHAR nomenclature (Hieble et al. Phar. Rev. 97:267 (1995)).

Pharmacological characteristics of $\alpha_1$ARs in human detrusor include a Kd for the radiolabeled $\alpha_1$AR antagonist [$^{125}$I] HEAT of 130±1.9 pM, similar to that reported for cells stably expressing the cloned human $\alpha_{1a}$AR subtype ((Schwinn et al, J Pharmacol. Exper. Ther. 272:134-142 (1995)). A representative saturation binding isotherm is shown in FIG. 2. Total $\alpha_1$AR density as measured by saturation binding in human detrusor membrane preparations with the $\alpha_1$AR antagonist [$^{125}$I]HEAT is 6.3±1.0 fmol/mg protein (mean±SEM, range 2.7-9.0, n=13). Although low (with corresponding high non-specific binding of 70-80% as expected), $\alpha_1$AR expression is reproducible and consistent within and between patients.

Example 3

Figure 3:
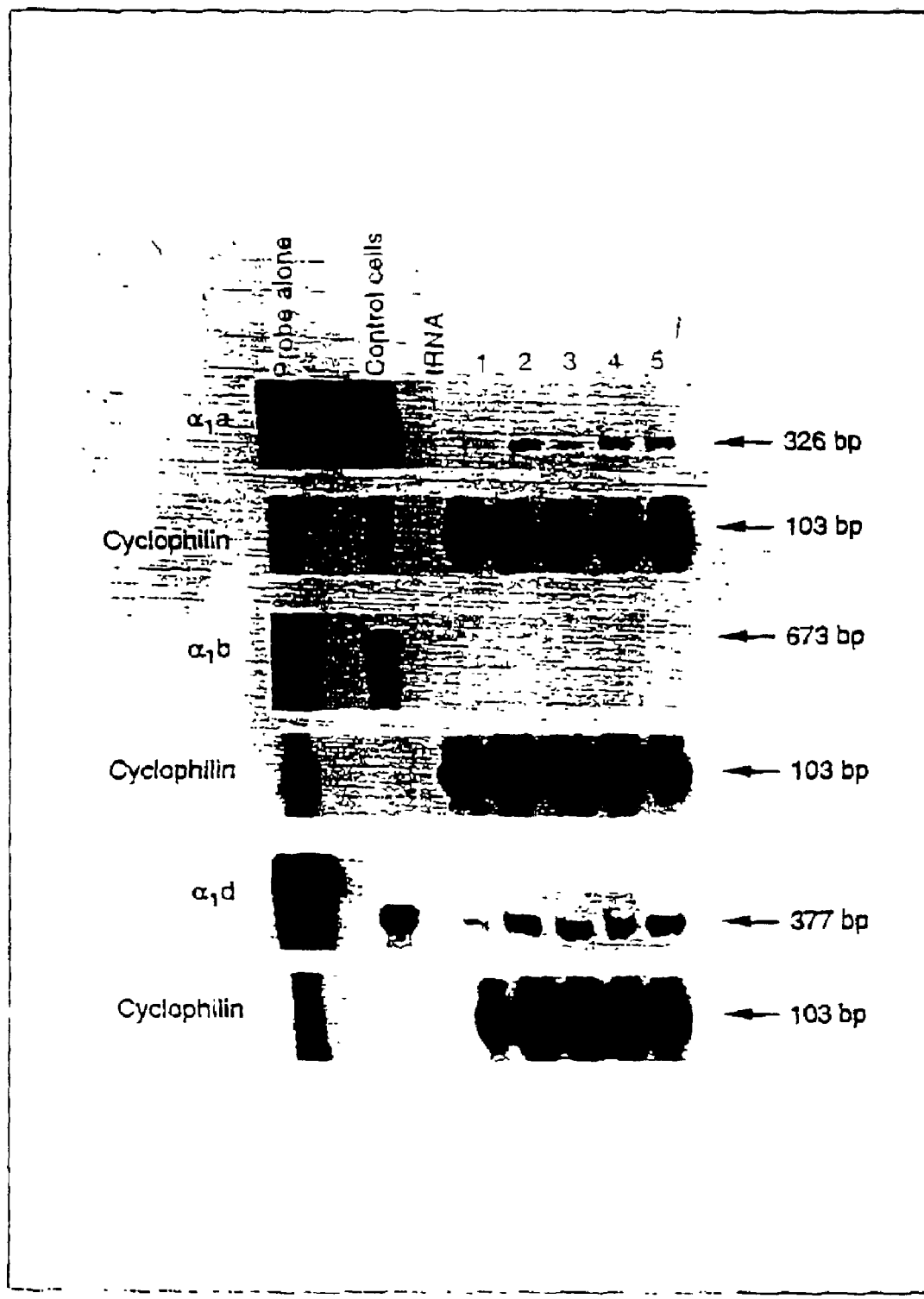
FIG. 3. RNase protection assays examining $\alpha_1$AR subtype expression in detrusor were performed in all patients (n=13). A representative RNase protection assay showing results from five patients is shown. In this experiment, radiolabeled probe for each $\alpha_1$AR subtype is shown at the far left along with (from left to right) protected fragments resulting from total RNA extracted from rat-1 fibroblast cells stably expressing each cloned human $\alpha_1$AR subtype (20 mg; positive probe control), yeast tRNA (20 mg; negative control); and total RNA isolated from human detrusor (20 mg) from five patients (lanes 1-5). Gel exposure times are 24 hrs for probe and positive control lanes and 72 hrs for tRNA and human detrusor samples. Although the $\alpha_{1a}$AR subtype mRNA band is stronger than the $\alpha_{1a}$AR protected fragment, the $\alpha_{1a}$AR probe contains 73% more radiolabeled αUTP compared with the $\alpha_{1d}$; hence, after normalization for radioactive label incorporation, two-fold predominance of the $\alpha_{1d}$AR subtype in human detrusor is apparent.

Identification and Quantification of the $\alpha_1$AR mRNA Subtypes in Human Bladder Detrusor In order to determine which $\alpha_1$AR subtypes are present in human detrusor, molecular approaches were chosen due to their sensitivity and specificity. To ensure specificity of the synthesized radiolabeled antisense human $\alpha_1$AR subtype selective probes. RNase protection assays were performed simultaneously with total RNA extracted from rat-1 fibroblast cells stably expressing each cloned human $\alpha_1$AR subtype. Each $\alpha_1$AR subtype specific probe protects a single predominant fragment of predicted size without cross-hybridization (FIG. 3. positive control cells); a lack of cross-hybridization between subtypes with each probe (Price et al, Mol. Pharmacol. 46:221-226 (1994)). As was previously demonstrated a further negative control, RFNase protection assays for each $\alpha_1$AR subtype selective probe were performed in tandom with yeast tRNA samples, where no hybridization is demonstrated (FIG. 3, tRNA lane). Human detrusor contains $\alpha_{1d}$AR >$\alpha_{1a}$AR mRNA, but no $\alpha_{1b}$AR mRNA in every patient studied (n=13; FIG. 3 shows representative results from patients number 1 through 5). This data, when corrected for background, normalized for cyclophilin content. and corrected for probe $^{32}$P-$\alpha$UTP incorporation. reveals that $\alpha_{1d}$AR mRNA constitutes 66±4.8% and $\alpha_{1a}$AR mRNA 34±4.8% of the total $\alpha_1$AR mRNA in human detrusor.

Example 4

Confirmation of $\alpha_1$AR Subtype mRNA in Human Detrusor and Comparison with Rat Whole Bladder using RT-PCR In order to confirm results from RNase protection assays and to compare with another frequently used animal model (rat), $\alpha_1$AR subtype expression was examined using RT-PCR in each patient. Primer nucleotide sequences, melting temperatures (T$_m$), and primer positions relative to the cDNA sequence are shown in Table 1 and Table 2; these primers do not span an intron.

TABLE 1

Oligonucleotide primers used for rat $\alpha_1$AR subtype RT-PCR.

| Rat $\alpha_1$AR primers | nucleotide sequences 5' 3' | T$_m$ | primer position relative to cDNA |
|---|---|---|---|
| $\alpha_{1a}$AR sense | GTAGCCAAGAGAAAGCCG | 62° C. | 628-647 |
| $\alpha_{1a}$AR antisense | CAACCCACCACGATGCCCAG | 66° C. | 839-820 |

TABLE 1-continued

Oligonucleotide primers used for rat α₁AR subtype RT-PCR.

| Rat α₁AR primers | nucleotide sequences 5' 3' | $T_m$ | primer position relative to cDNA |
|---|---|---|---|
| $\alpha_{1b}$AR sense | GCTCCTTCTACATCCCGCTCG | 68° C. | 629-649 |
| $\alpha_{1b}$AR antisense | AGGGGAGCCAACATAAGATGA | 62° C. | 928-908 |
| $\alpha_{1d}$AR sense | CGTGTGCTCCTTCTACCTACC | 66° C. | 759-779 |
| $\alpha_{1d}$AR antisense | GCACAGGACGAAGACACCCAC | 68° C. | 1062-1042 |

The nucleotide sequence listed above correspond to the following sequence identifiers, respectively: SEQ ID Nos:1-6.

TABLE 2

Oligonucleotide primers used for human α₁AR subtype RT-PCR.

| Human α₁AR primers | nucleotide sequences 5' 3' | $T_m$ | primer position relative to cDNA |
|---|---|---|---|
| $\alpha_{1a}$AR sense | ATCATCTCCATCGACCGCTACA | 66° C. | 355-376 |
| $\alpha_{1a}$AR antisense | TCACTTGCTCCGAGTCCGACTT | 68° C. | 697-676 |
| $\alpha_{1b}$AR sense | GCTCCTTCTACATCCCTCTGG | 68° C. | 629-649 |
| $\alpha_{1b}$AR antisense | AGGGTAGCCAGCACAAGATGA | 67° C. | 928-908 |
| $\alpha_{1d}$AR sense | ACCACGCGCAGCCTCGAGGCAGGC | 84° C. | 850-873 |
| $\alpha_{1d}$AR antisense | GAGCGAGCTGCGGAAGGTGTGGCC | 82° C. | 999-976 |

The nucleotide sequence listed above corresponds to the following sequence identifiers, respectively: SEQ ID NOs:7-12.

Figure 4:
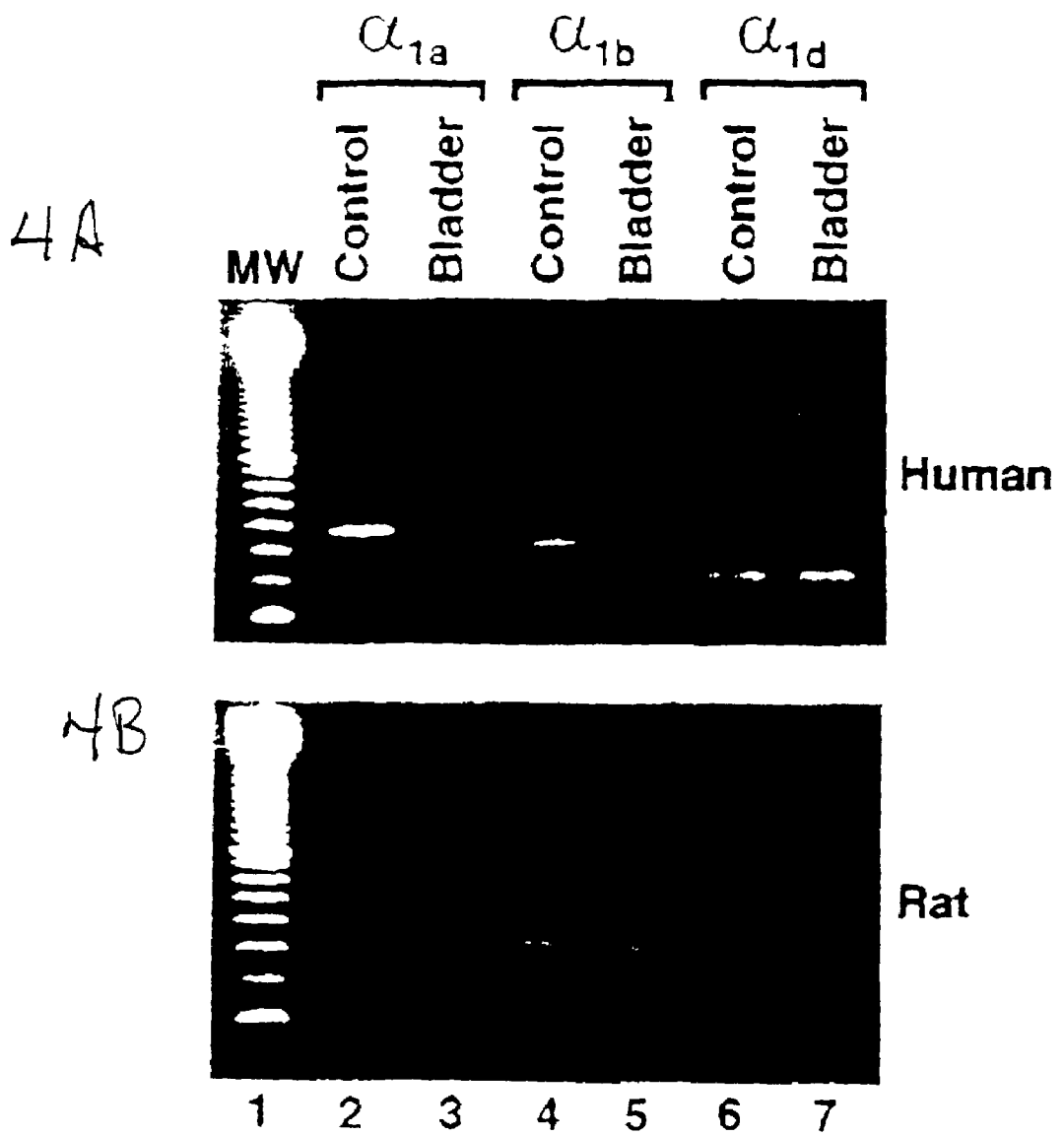
FIGS. 4A and 4B. Results from RT-PCR experiments on human detrusor (FIG. 4A) and rat whole bladder (FIG. 4B) RNA. $\alpha_{1d}$AR subtype specific cDNA in plasmid vectors served as positive controls.

Although RNase protection assays are considered the "gold standard" for quantitating mRNA present in a given tissue, this approach is not as sensitive as PCR, therefore very small amounts of mRNA can be missed in a RNase protection assay but demonstrated by PCR. As shown in FIG. 4, RT-PCR performed on human detrusor total RNA demonstrates the presence of $\alpha_{1a}$AR and $\alpha_{1d}$AR mRNA, and lack of $\alpha_{1b}$AR mRNA, consistent with data from the RNase protection assays. Of note, $\alpha_{1d}$AR mRNA accounts for approximately 60-70% of total $\alpha_1$AR mRNA in human derrusor with $\alpha_{1a}$AR mRNA accounting for 30-40%. again confirming the RNase protection assay results. Species heterogeneity (human versus rat) of $\alpha_1$AR subtype mRNA expression has been previously reported for many tissues (Price et al, Mol. Pharmacol. 46:221-226 (1994), Price et al, Mol. Pharmacol. 45:171-175 (1994)). Indeed, as seen in FIG. 4, RT-PCR performed on pooled rat bladder total RNA demonstrates the presence of all three $\alpha_1$AR mRNAs in roughly equal concentrations in rat.

Example 5

Determination of $\alpha_1$AR Subtype Expression at a Protein Level

Figure 5:
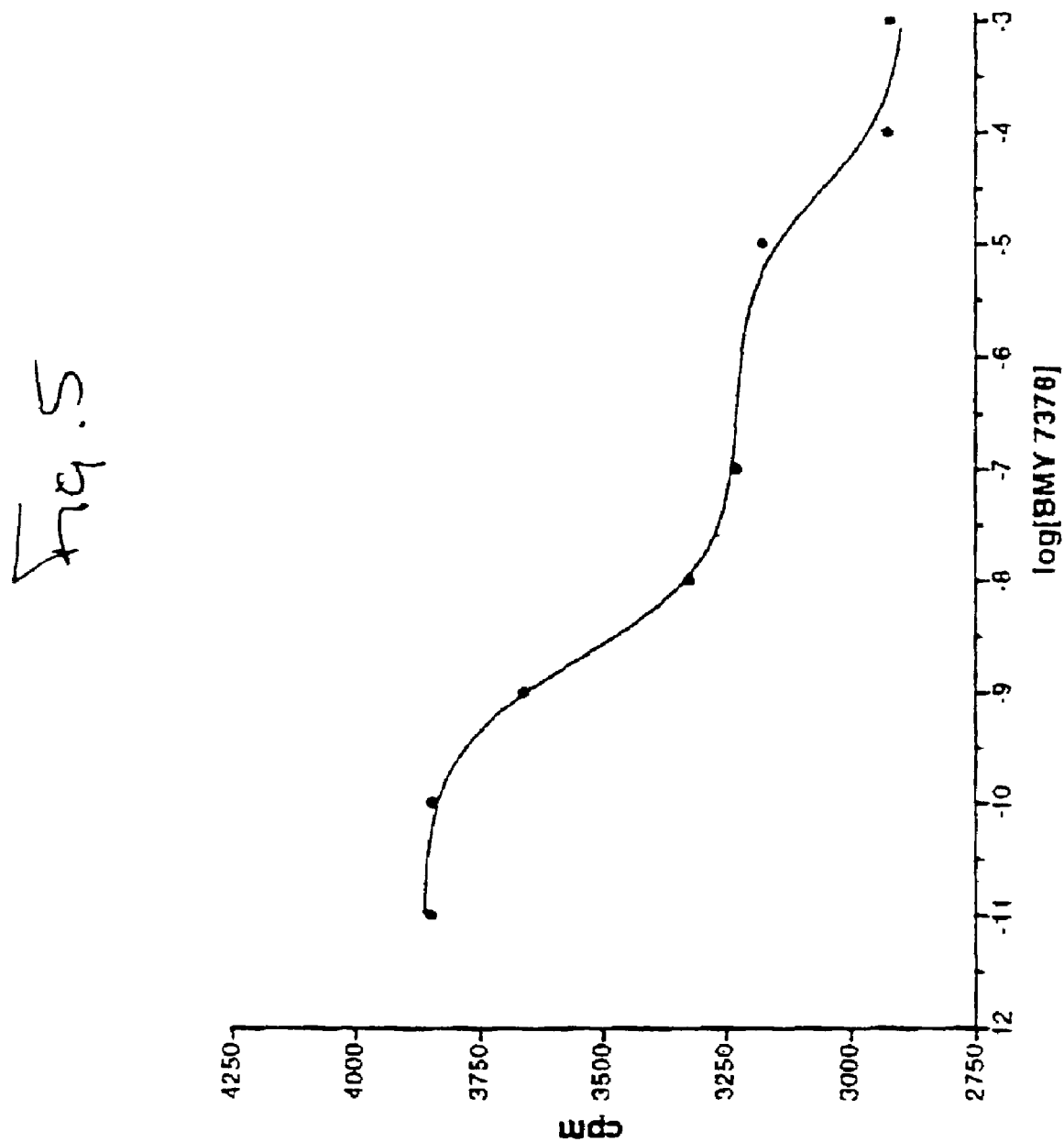
FIG. 5. $\alpha_1$AR subtype expression in human detrusor was determined using competition analysis with the $\alpha_{1d}$AR-subtype selective ligand BMY7378. Results from a representative curve are shown demonstrating a two-site fit with high affinity Ki corresponding to the $\alpha_{1d}$AR.

Competition analysis was used to determine $\alpha_1$AR subtype expression at a protein level in human detrusor. Since molecular studies demonstrate a predominance of $\alpha_{1d}$AR mRNA, the $\alpha_{1d}$AR -selective compound BMY7378 was used in these studies. As graphically represented in FIG. 5, a two-site fit was evident in every patient studied (n=13), with high affinity binding predominating (high $pK_i$, =8.6±0.2 [66±3.1% total] vs. low $pK_i$, =4.9±0.2 [35±3.1% total]) (Table 3).

TABLE 3

Results from competition binding experiments utilizing membranes from rat-1 fibroblasts stably transfected with each $\alpha_1$AR subtype (controls) and human detrusor (n = 13). Since no $\alpha_{1b}$AR was found in human detrusor by RNase protection assays and RT-PCR, one versus two site fit of the data was utilized.

| | BMY7378 ($pK_i$) | | | | |
|---|---|---|---|---|---|
| | $\alpha_{1a}$AR | $\alpha_{1b}$AR | $\alpha_{1d}$AR | % High | % Low |
| Human detrusor | 4.9 ± 0.2 | — | 8.6 ± 0.2 | 66 ± 3.1 | 35 ± 3.1 |
| Control $\alpha_{1a}$ | 4.8 ± 0.1 | — | — | | |
| Control $\alpha_{1b}$ | — | 5.1 ± 0.3 | — | | |
| Control $\alpha_{1d}$ | — | — | 8.5 ± 0.1 | | |

All documents cited above are hereby incorporated in their entirety by reference.

One skilled in the art will appreciate from a reading of this disclosure that various changes in form and detail can be made without departing from the true scope of the invention.

What is claimed is:

1. A method of treating irritative symptoms of bladder or lower urinary tract disease comprising administering to a patient in need of such treatment an effective amount of a construct comprising an oligonucleotide that inhibits production of $\alpha_{1d}AR$ or that encodes a molecule that inhibits production of $\alpha_{1d}AR$.

2. The method according to claim 1 wherein said construct is an antisense construct.

* * * * *

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 1
gtagccaaga gaaagccg                                                          18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
caacccacca cgatgcccag                                                        20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
gctccttcta catcccgctc g                                                      21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
aggggagcca acataagatg a                                                      21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 5
cgtgtgctcc ttctacctac c                                                      21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 6
gcacaggacg aagacaccca c                                                      21

<210> SEQ ID NO 7
<211> LENGTH: 22

```
<212> TYPE: DNA
<213> ORGANISM: Artificial Sequence
<220> FEATURE:
<223> OTHER INFORMATION: Description of Artificial Sequence: primer

<400> SEQUENCE: 7
atcatctcca tcgaccgcta ca                                              22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
tcacttgctc cgagtccgac tt                                              22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
gctccttcta catccctctg g                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 10
agggtagcca gcacaagatg a                                               21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 11
accacgcgca gcctcgaggc aggc                                            24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 12
gagcgagctg cggaaggtgt ggcc                                            24
```